United States Patent
Delamarche et al.

(10) Patent No.: US 10,112,193 B2
(45) Date of Patent: Oct. 30, 2018

(54) FABRICATION OF A MICROFLUIDIC CHIP PACKAGE OR ASSEMBLY WITH SEPARABLE CHIPS

(71) Applicant: International Business Machines Corporation, Armonk, NY (US)

(72) Inventors: Emmanuel Delamarche, Rueschlikon (CH); Yuksel Temiz, Rueschlikon (CH)

(73) Assignee: International Business Machines Corporation, Armonk, NY (US)

( * ) Notice: Subject to any disclaimer, the term of this patent is extended or adjusted under 35 U.S.C. 154(b) by 183 days.

(21) Appl. No.: 14/901,685

(22) PCT Filed: Jun. 18, 2014

(86) PCT No.: PCT/IB2014/062346
§ 371 (c)(1),
(2) Date: Dec. 28, 2015

(87) PCT Pub. No.: WO2014/207619
PCT Pub. Date: Dec. 31, 2014

(65) Prior Publication Data
US 2016/0367984 A1   Dec. 22, 2016

(30) Foreign Application Priority Data
Jun. 28, 2013   (GB) .................................. 1311680.1

(51) Int. Cl.
*B01L 3/00*         (2006.01)
*H01L 21/00*        (2006.01)
(Continued)

(52) U.S. Cl.
CPC .... *B01L 3/502707* (2013.01); *B81C 1/00888* (2013.01); *B01L 2300/044* (2013.01);
(Continued)

(58) Field of Classification Search
CPC ............. B01L 3/00; H01L 21/00; H01L 21/46
(Continued)

(56) References Cited

U.S. PATENT DOCUMENTS 5,063,081 A    11/1991  Cozzette et al.
5,885,470 A *  3/1999   Parce .................. B01J 19/0093
                                                 204/450

(Continued)

FOREIGN PATENT DOCUMENTS

DE    10 2008 001 95 A1    11/2009
JP       2011215006 A       10/2011

OTHER PUBLICATIONS

Gervais et al., "Toward one-step point-of-care immunodiagnostics using capillary-driven microfluidics and PDMS substrates", The Royal Society of Chemistry 2009, Lab Chip, 2009, vol. 9, No. 23, Dec. 7, 2009, pp. 3313-3452.

(Continued)

Primary Examiner — Brian J. Sines
(74) Attorney, Agent, or Firm — Scully, Scott, Murphy & Presser, P.C.; David Quinn, Esq.

(57) ABSTRACT

The present invention is notably directed to methods of fabrication of a microfluidic chip package or assembly (1), comprising: providing (S1) a substrate (10, 30) having at least one block (14, 14a) comprising one or more microfluidic structures on a face (F) of the substrate; partially cutting (S2) into the substrate to obtain partial cuts (10c), such that a residual thickness of the substrate at the level of the partial cuts (10c) enables singulation of said at least one block (14, 14a); cleaning (S4) said at least one block; and applying (S5-S7) a cover-film (62) to cover said at least one block (14, 14a), whereby at least one covered block is obtained, the applied cover film still enabling singulation of each covered block, wherein each covered block corresponds to a microfluidic chip after singulation. The present invention is further (Continued)

directed to microfluidic chips, packing or assembly, obtainable with such methods.

10 Claims, 5 Drawing Sheets

(51) Int. Cl.
 *H01L 21/46* (2006.01)
 *B81C 1/00* (2006.01)
 *G01N 33/487* (2006.01)
(52) U.S. Cl.
 CPC ............ *B01L 2300/0627* (2013.01); *B01L 2300/0816* (2013.01); *B01L 2300/0883* (2013.01); *B01L 2300/0887* (2013.01); *G01N 33/487* (2013.01)
(58) Field of Classification Search
 USPC ........ 422/502, 503; 264/650, 655, 678, 118, 264/602, 643, 129, 131, 338; 438/48, 49, 438/33, 68, 113, 114, 458, 460
 See application file for complete search history.

(56) References Cited

U.S. PATENT DOCUMENTS

| | | | |
|---|---|---|---|
| 6,425,972 | B1 | 7/2002 | McReynolds |
| 6,830,990 | B1 | 12/2004 | Honer et al. |
| 8,466,042 | B2 | 6/2013 | Laermer et al. |
| 2005/0266582 | A1* | 12/2005 | Modlin ................. B01L 3/5027 436/164 |
| 2007/0141805 | A1* | 6/2007 | Chang ............... B01L 3/502707 438/456 |
| 2008/0219894 | A1* | 9/2008 | Ganesan ........... B01L 3/502715 422/82.12 |
| 2011/0163398 | A1 | 7/2011 | Laermer et al. |
| 2014/0227818 | A1* | 8/2014 | Binder ................. G01L 9/0052 438/52 |

OTHER PUBLICATIONS

Sollier et al., "Rapid prototyping polymers for microfluidic devices and high pressure injections", The Royal Society of Chemistry 2011, Lab Chip 2011, vol. 11, accepted Sep. 9, 2011, pp. 3752-3765.

\* cited by examiner

FABRICATION OF A MICROFLUIDIC CHIP PACKAGE OR ASSEMBLY WITH SEPARABLE CHIPS

FIELD OF THE INVENTION

The invention relates in general to the fabrication of microfluidic chip package or assembly. It is in particular directed to methods of fabrication of several microfluidic chips on a same wafer.

BACKGROUND OF THE INVENTION

Microfluidics generally refers to microfabricated devices, which are used for pumping, sampling, mixing, analyzing and dosing liquids. Prominent features thereof originate from the peculiar behavior that liquids exhibit at the micrometer length scale. Flow of liquids in microfluidics is typically laminar. Volumes well below one nanoliter can be reached by fabricating structures with lateral dimensions in the micrometer range. Reactions that are limited at large scales (by diffusion of reactants) can be accelerated. Finally, parallel streams of liquids can possibly be accurately and reproducibility controlled, allowing for chemical reactions and gradients to be made at liquid/liquid and liquid/solid interfaces. Microfluidics are accordingly used for various applications in life sciences. Microfluidic devices microfluidic are commonly called microfluidic chips.

For example, microfluidic-based bioassays require passing a liquid sample inside a microfluidic flow path. The flow conditions (volume passing and flow rate) are important as they impact the outcome of the assay. While several methods and devices for flowing liquids inside microfluidic flow paths have been developed, these methods either lack flexibility or operate with a limited type of samples and flow conditions.

Besides, the fabrication of microfluidic chips using semiconductor wafers such as Si wafers seems attractive: one may expect to benefit from a range of existing processes, as continuously developed in the past decades for integrated circuits, to obtain accurate microfluidic structures. However, contrary to what is done in semiconductor wafer processing, microfluidics generally have deep structures, i.e., around a few micrometer, up to 20 micrometers or even deeper. In many cases, 5 micrometers is already considered as a small depth in microfluidic applications because such a small depth can generate a large hydraulic resistance on a liquid and can block or become clogged with microbeads and particles, such a small depth can also be incompatible with samples containing cells. As a result, existing semiconductor wafer processes are challenged by, if not incompatible with the requirements needed for microfluidic chip fabrication both in terms of manufacturing processes and cost of fabrication.

BRIEF SUMMARY OF THE INVENTION

According to a first aspect, the present invention is embodied as a method of fabrication of a microfluidic chip package or assembly, comprising:
  providing a substrate having at least one block comprising one or more microfluidic structures on a face of the substrate;
  partially cutting into the substrate to obtain partial cuts, such that a residual thickness of the substrate at the level of the partial cuts enables singulation of said at least one block;
  cleaning said at least one block; and
  applying a cover-film to cover said at least one block, whereby at least one covered block is obtained, the applied cover film still enabling singulation of each covered block, wherein each covered block corresponds to a microfluidic chip after singulation.

Typically, the substrate provided has several blocks, each comprising one or more microfluidic structures on a face of the substrate; the applied cover-film covers said several blocks; and the partial cuts obtained and the cover-film applied are such as to enable singulation of each of said several blocks.

Preferably, partially cutting into the substrate is carried out such that a residual thickness of the substrate after partially cutting makes it possible to separate said at least one block by hand, preferably by cleaving said at least one block.

In preferred embodiments, the cover-film applied comprises openings forming patterns corresponding to structures of the microfluidic chip assembly already present or to be subsequently fabricated.

Preferably, the cover-film applied is a dry-film resist, and, preferably, the cover-film fulfills one or more of the following conditions: it comprises an epoxy resin, it is a laminate sheet, and has a Young's modulus between 3 and 5 gigapascal.

In embodiments, a thickness of the dry-film resist applied is between 10 and 100 μm, and preferably between 30 and 70 μm.

Preferably, applying the cover film comprises: providing a film comprising at least two layers, including the cover film and a backing film; applying the cover film against an exposed surface on said face of the substrate by pressing the backing film, preferably by laminating the backing film; and removing the backing film.

In preferred embodiments, providing the film further comprises patterning the cover film, preferably by one of: photolithography; cutting; punching; or laser ablation, prior to applying the patterned cover film, to obtain a cover film that comprises openings forming patterns corresponding to structures of the microfluidic chip assembly already present or to be subsequently fabricated.

Preferably, at least one block of the substrate provided exhibits a microfluidic microchannel on said face, the average depth or cross-sectional diameter of the microchannel being between 5 and 50 micrometers, and preferably between 10 and 20 micrometers.

In embodiments, the method further comprises, after cleaning and before applying the cover-film, a step of depositing reagents in one or more of the microfluidic structures, wherein depositing reagents preferably comprises depositing at least two types of reagents in microfluidic structures of at least two different blocks of the substrate, respective, or within one or more microstructures of a same block.

According to another aspect, the invention is embodied as a microfluidic chip package or assembly comprising:
  a substrate having one or more blocks, each comprising one or more microfluidic structures on a face of the substrate, wherein the substrate comprises one or more partial cuts extending in a thickness of the substrate, such that a residual thickness of the substrate at the level of the partial cuts enables singulation of each of said one or more blocks, preferably by hand; and
  a cover-film covering said one or more blocks, thereby forming one or more covered blocks, the applied cover film being such as to enable singulation of each of said one or more covered blocks, each covered block corresponding to a microfluidic chip after singulation.

In preferred embodiments, the cover film is a dry-film resist and has a thickness between 20 and 100 µm, preferably between 30 and 70 µm.

Preferably, the cover film comprises openings forming patterns corresponding to microfluidic structures of the one or more blocks, said microfluidic structures being one or more of:
an electrical contact opening;
a liquid loading pad; and
an air vent.

According to still another aspect, the invention is embodied as a use of such a microfluidic chip package or assembly, wherein: the microfluidic chip assembly is provided to a recipient; and the recipient separates at least one of said one or more blocks from the assembly.

According to a final aspect, the invention is embodied as a microfluidic chip obtainable according to the above methods or from the above microfluidic chip packages or assemblies, by separating a covered block from the package or assembly, the chip comprising a covered block and exhibiting residual marks of partial cut and residual marks of singulation, such as cleavage planes or parting breaks, at a periphery thereof.

Devices and methods embodying the present invention will now be described, by way of non-limiting examples, and in reference to the accompanying drawings. Technical features depicted in the drawings are not necessarily to scale.

DETAILED DESCRIPTION OF THE INVENTION

The following description is structured as follows. First, general embodiments and high-level variants are described (sect. 1). The next section addresses more specific embodiments and technical implementation details (sect. 2).

1. General Embodiments and High-Level Variants

Figure 1:
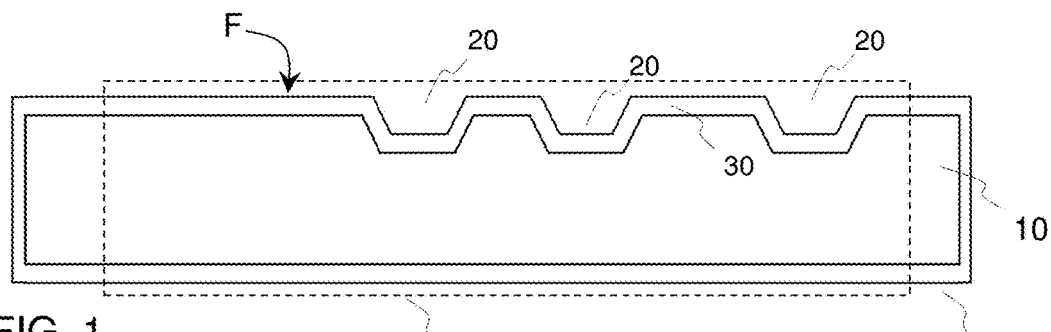
FIGS. 1 to 8 schematically illustrate high-level steps of methods of fabrication, according to embodiments. Each step is illustrated using a schematic, partial depiction of a cross-section of a chip package or assembly, focusing on one block thereof.
Figure 1A:
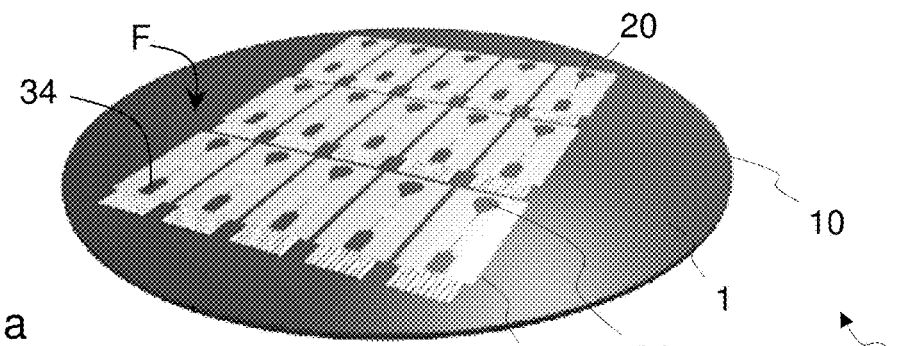
FIGS. 1a, 2a, 5a and 8a are 3D (schematic) views corresponding to FIGS. 1, 2, 5 and 8 respectively.

In reference to FIGS. 1-11, an aspect of the invention is first described, which concerns methods of fabrication of a microfluidic chip package or assembly 1. Essentially, these methods revolve around the following steps:

1. First, a substrate 10, 30 is provided, step S1 (FIGS. 1, 1a). The substrate exhibits one or (more likely) more blocks 14, 14a. Each block comprises one or more microfluidic structures 20, 24, 34 visible on a main face F of the substrate. Such microstructures are assumed to be already machined or patterned at this stage of the process, e.g., according to methods known in the art. In the following, it is generally assumed that several blocks are present, subject to an exception that concerns the fabrication of specific packages. When several blocks are present, present fabrication methods concern to the fabrication of an assembly of microfluidic chips. The concept of "microfluidic structures" (also "microstructures" or "microfluidic features") is widely used in the present technical field to denote such features as: microfluidic microchannels 20; liquid loading pads 24; electrical contact openings, capillary pumps 34, etc. Examples of such microfluidic structures are visible in the blocks depicted notably in FIG. 1a.
2. Second, one partially cuts, step S2 (FIG. 2, FIG. 2a), into the substrate 10, 30 to obtain partial cuts 10c. One may speak of partial dicing too. The partial cuts 10c obtained are such that a residual thickness 10r of the substrate at the level of the partial cuts 10c enables singulation of the blocks 14, 14a.
3. Then, blocks and microstructures therein are cleaned, step S4 (FIG. 4), using any suitable methods; and
4. Finally, a cover-film 62 is applied (step S5-S7, FIGS. 5-7) to cover said blocks 14, 14a, e.g., to seal microstructures in the blocks. This cover film should not be confused with a protective film that one may want to use to protect the chip assembly before cutting. In particular, the cover film should be rigid enough to tent over the microstructures without collapsing therein. This cover film should otherwise appropriately complete the microstructures and not impair the microfluidic functionality of the chips. Still, the cover film is chosen such that the applied cover film still enables singulation of each block, e.g., it should be brittle enough to that aim.

At this point, an assembly of chips is obtained (or a package, if only one block is present), which can be provided to a user for subsequent singulation (step S8) of the blocks. Each covered block shall correspond to a microfluidic chip (possibly ready for use), after singulation.

Figure 2:
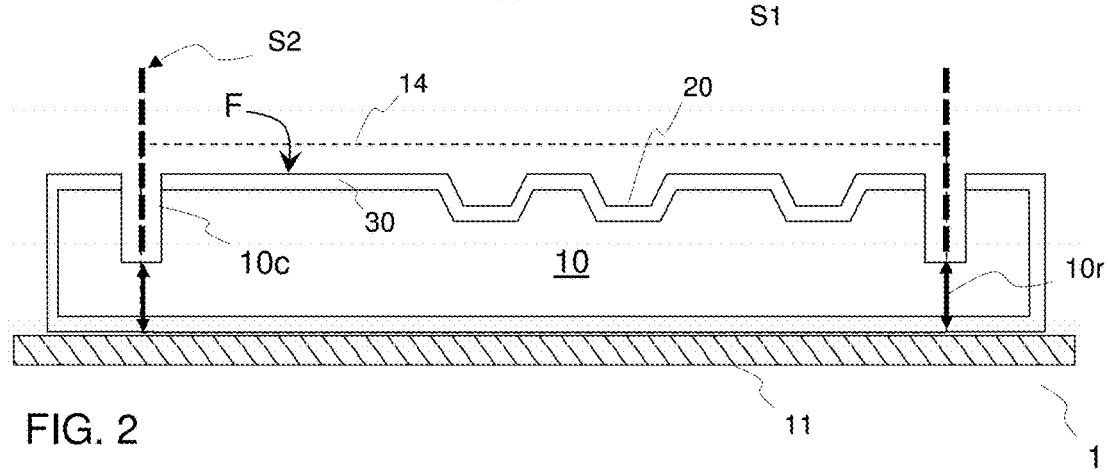
Figure 2A:
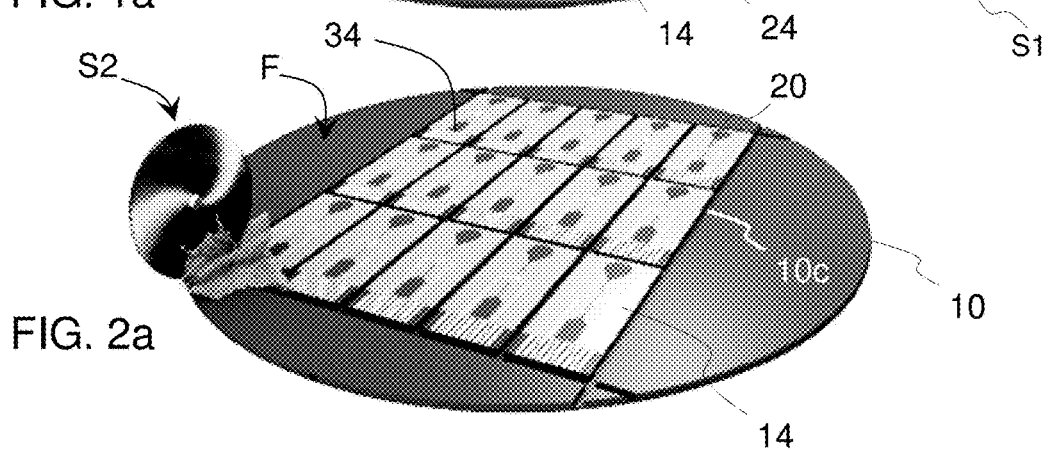
Figure 8A:
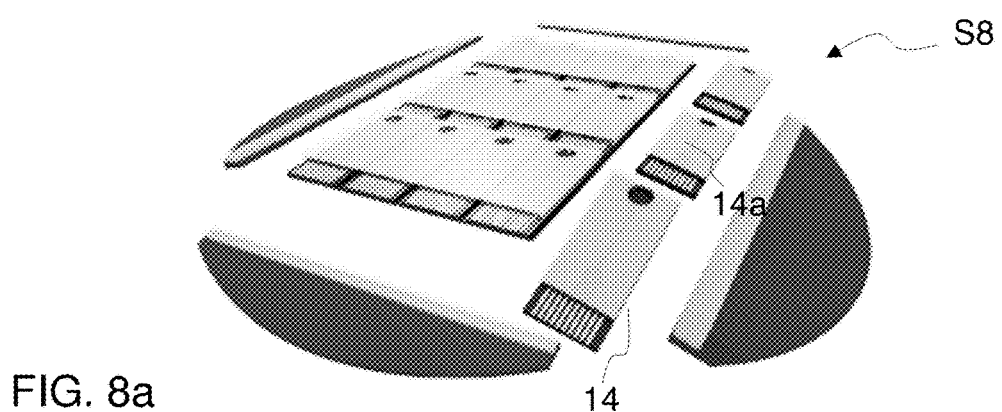
Figure 4:
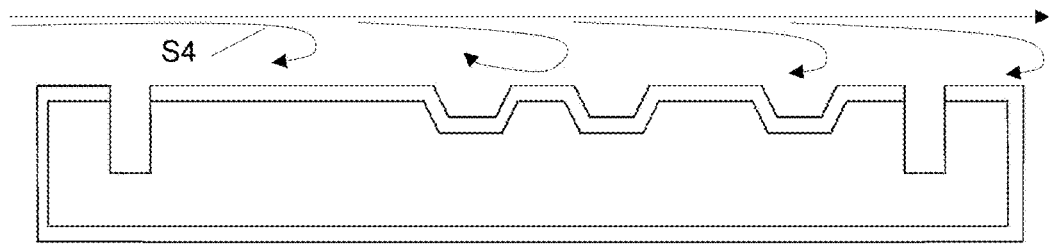
Figure 4A:
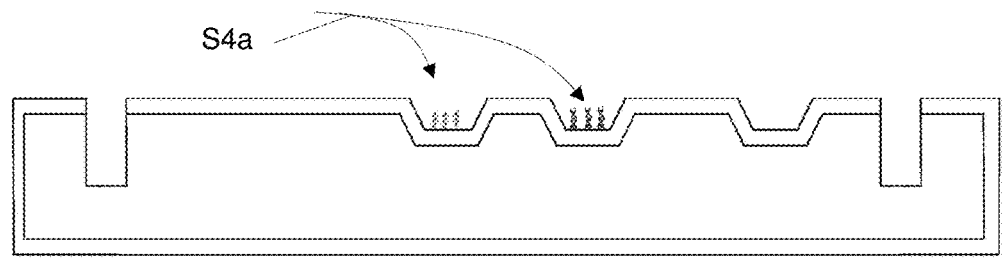

At step S2: "cutting" is to be interpreted broadly: the partial cut may be carried out by mechanically sawing e.g., using a dicing saw (as depicted in FIG. 2a), wire saw, etc., or still by scribing or laser cutting, etc. The cutting step S2 can typically be carried out by cutting transversely to an average plane of the substrate. It gives rise to partial cuts 10c extending into the thickness of the substrate 10, 30, and notably into the thickness of a main component, e.g., a main body 10 of the substrate.

The partial cut is preferably carried out from above (as illustrated in FIG. 2a), from the same side exhibiting the microstructures; the uncut residual portion 10r is a lower portion in that case. In more details, it is advantageous, for opaque substrates such as silicon, to carry out the partial cut from above, in order to more easily align the dicing to the microstructures or the dicing marks, e.g., with the help of a camera present in the dicing tool. The regions to be cut can be marked by patterns (dicing marks) fabricated during the microchannel or microelectrode (if present) fabrication. For transparent substrates, such as Pyrex, Glass, etc., the cutting can be carried out from either side since the dicing marks are visible from both sides. In this case, the exposed side F of the substrate may not have to be protected by an additional protective film since the dicing tape may already act as such.

Besides, step S2 implicitly involves cutting along a periphery of the blocks, i.e., to later enable singulation thereof, as best seen in FIG. 2a. However, depending on the material chosen for the substrate, it may not be necessary to cut along the entire periphery of the blocks, as long as the cut lines 10c enable subsequent singulation of the blocks. For example, contiguous dashed cut lines may suffice, the cuts being through holes or not, but this would substantially complicate the cutting step. Thus, it is preferred to obtain cuts 10c (step S2) that are partial in the thickness of the substrate, as illustrated in FIG. 2 or 2a (and contrary to the usual dicing), and at least partial in-plane, though preferably extending along the entire periphery of the blocks, as depicted in FIG. 2a. As illustrated in FIG. 2a, most efficient is to partially cut along lines forming an array, which array delimitates the blocks 14, 14a. Since partial cuts of the substrate are contemplated, the substrate is still single-piece after step S2; blocks 14, 14a are typically level with each other. On the contrary, in wafer-level processing, dicing usually means separating dies from a wafer following wafer processing, i.e., the wafer is fully cut through.

The substrate is preferably an essentially planar, typically layered support structure comprising, in addition to a main body 10 (e.g., a wafer), one or more layers 30, 32 covering the body 10. Layers 30 typically comprise thin layers, which may comprise a material such as a metal or an oxide, i.e., distinct from the material of the body 10. The substrate may further comprise a layer 32 such as a photopatterned dry-film resist 32 (e.g., PerMX3020) or patterned photoresist, for example SU-8, in which microfluidic structures 20 are defined. For the sake of clarification, in FIGS. 1-8, microstructures are assumed to be grooved, e.g., etched, in the substrate 10, 30, whereas in the embodiment of FIG. 11, microstructures such as microchannel 20 are defined in a photopatterned dry-film resist 32.

The body 10 is preferably mounted on a dicing tape 11 prior to cutting S2, the dicing tape opposite to the microfluidic structures. The tape 11 may have a sticky backing to hold the body 10, e.g., on a thin sheet metal frame. The dicing tape 11 may more generally be any structure supporting the body 10, to hold and preserve the body while cutting S2. The tape 11 is typically removed after cutting S2 as it is usually not compatible with cleaning solvents. A protective photoresist layer may be applied before cutting, e.g., for protection; and if so, it shall be removed before or during cleaning.

The whole substrate can be cleaned, step S4, after cutting. The cleaning step S4 shall preferably involve rinsing and drying the substrate as well. Also, at this point, the assembly 1 including any microstructure thereon may undergo a surface treatment, be functionalized, etc., depending on the application desired.

The following steps S5-S7 aim at applying a cover-film to cover the microfluidic structures and possibly complete them e.g., close the channels 20 in each block. Preferably, a single cover film is applied to cover all microstructures on the substrate, though multiple layers can be contemplated too, if necessary. The cover film 62 is thus applied at substrate-level too, after partially cutting S2 and cleaning S4, and before any subsequent singulation step S8. As said earlier, the cover film 62 must be distinguished from a protective photoresist film that can otherwise be applied before cutting S2 and removed after. Indeed, protective films are usually applied before dicing to protect a processed wafer. Since here the cover film 62 is applied after cutting and cleaning (e.g., after having rinsed, cleaned and dried) the partially cut substrate, clean microfluidic structures are obtained for the whole assembly, i.e., at substrate level, a thing that so far was only carried out at chip level. The above solution is all the more advantageous when cutting S2, cleaning S4, surface treatment (if any) and reagent integration S4a (if any), e.g., any one or more of the steps occurring prior to sealing, is to be carried out in a wet environment. Once the exposed surface is sealed with the cover film 62, the assembly can be singulated and the resulting dies can be readily used.

It is worth noting that in the case of using the chip for biological applications such as diagnostics, the chip and cover can also be sterilized using chemicals such as 70% ethanol before sealing the chip and chip singulation. Therefore, the risk of adversary filling of liquids into the closed channels during cutting and surface preparation is prevented.

Of particular interest is the possibility to deposit reagents in the microfluidic structures after the partial cut S2 and cleaning S4. The method may thus comprise an intermediate step S4a of depositing reagents in one or more of the microfluidic structures e.g., microchannels. Correspondingly, devices according to embodiments may include such reagents in microstructures. To that aim, one may for instance add solutions containing reagents in microchannels using an inkjet spotter and dry the reagents. Lamination of a dry film resist at low temperature (e.g., approximately 45 degrees) is then ideal because this process will not significantly damage reagents such as proteins. An opportunity is thus offered for integrating reagents before covering the device with the cover-film 62. Different reagents could be deposited in respective blocks 14, 14a, or even within different microstructures 20 of a same block. This opportunity opens the way to large-scale production of biochemically functionalized microfluidic devices.

As touched earlier, the substrate 10, 30 preferably has several blocks 14, 14a, which comprise, each, microfluidic structures (machined or otherwise provided on face F of the substrate, FIGS. 1, 1a. In that case, the applied cover-film 62 covers all blocks 14, 14a. The partial cuts 10c obtained and the cover-film 62 applied are such as to still enable singulation of the blocks 14, 14a. In variants, only one block is provided; an the method restricts to the fabrication of a specific package in that case, where outer lateral portions of substrate, i.e., beyond the partial cuts, serve to better protect, manipulate and transport the unique block in that case.

Figure 9:
FIG. 9 is a photograph illustrating a singulation of one chip, as otherwise illustrated in FIG. 8), and as involved in embodiments.

Referring now more specifically to FIG. 9, the step of partially cutting S2 into the substrate is preferably carried out such that a residual thickness 10r of the substrate after partially cutting S2 makes it possible to separate the blocks by hand, e.g., by cleaving the blocks 14, 14a. The body 10, e.g., a Si wafer, typically is the main mechanical support of the chip assembly, such that mechanical properties of the assembly (starting with robustness) are mainly determined by the body 10. Thus, the residual thickness 10r, after cutting S2, of the body 10 (and more generally of the substrate 10, 30 as a whole) at the level of the partial cuts 10c must be such as to enable subsequent singulation by hand in that case.

Since several chips are manufactured from a same wafer, for efficiency, partial cuts are carried out around each block 14, 14a, see FIG. 2a. The residual thickness 10r of the body 10 after cutting can be tuned (FIG. 2), depending on the materials involved, to make it cleavable by hand: any user could thus proceed to the singulation, as illustrated in FIG.

9. Lateral assemblies of chips, i.e., blocks 14, 14a can thus be provided to users as a single object. The user can then separate the blocks without any equipment. As evoked earlier, in variants, a single block 14 could be provided to a user, surrounded by inactive lateral substrate portions, which are partially separated from the single block by partial cuts 10c that enable singulation.

The partial cuts are preferably obtained at the level of an inactive region. Yet, further optimization of the manufacture process may lead to design some of the functional features extending from one block 14 to another, contiguous block 14a, such as electrical contacts or air vents, which can possibly be cut S2, e.g., in halves. This provides, in fine, electrical contacts, air vents, etc. for two or more contiguous dies, a thing that may simplify the manufacture steps and allows for saving space on the initial substrate.

Tests done with Si wafers or with glass substrates led to conclude that the residual thickness (call it $t_r$) of the body 10 after partially cutting S2 should preferably be close to half the initial thickness (or $t_i$), i.e., as of before partially cutting (appended drawings are not necessarily to scale). For instance, most satisfactory results were obtained for $t_r = x \, t_i$, with $x \in [0.43\text{-}0.52]$. Otherwise the body may not be robust enough and break during subsequent fabrication steps, i.e., cleaning, cover film lamination, etc., as present inventors have concluded. On the other hand, the residual thickness should not be too large, for allowing a user to singulate the chips. Note that the initial wafer thickness $t_i$ typically depends on the wafer size e.g., 525 µm for 4-inch wafers to 775 µm for 12-inch wafers. Best results have for instance been obtained for 4-inch Si wafers that had been partially cut to about 250-300 µm. A satisfactory trade-off typically is to obtain residual thicknesses that after partially cutting are less than 500 µm, and more preferably less than 300 µm for Si wafers. For glass wafers, a 300 to 350 µm cutting depth, typically 50 µm more than for a Si wafer, is preferred, to achieve easier breaking as glass does not have crystallographic planes.

Figure 3:
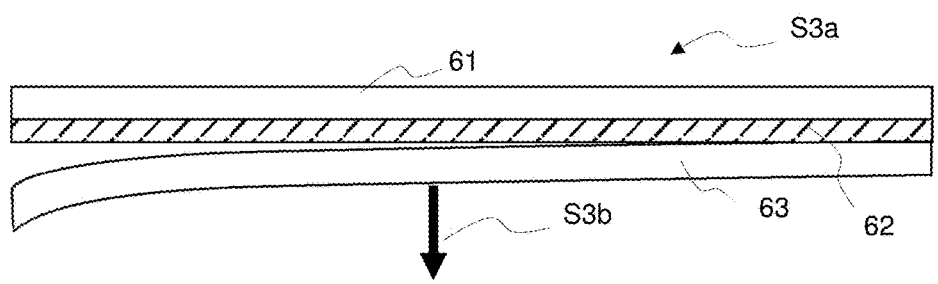
Figure 3:
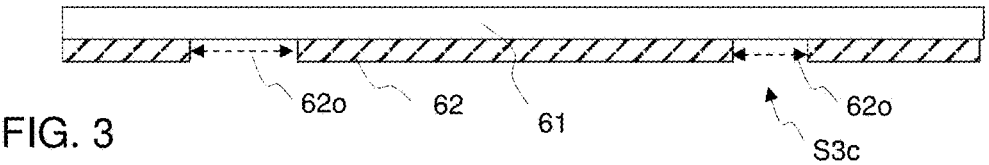
Figure 5A:
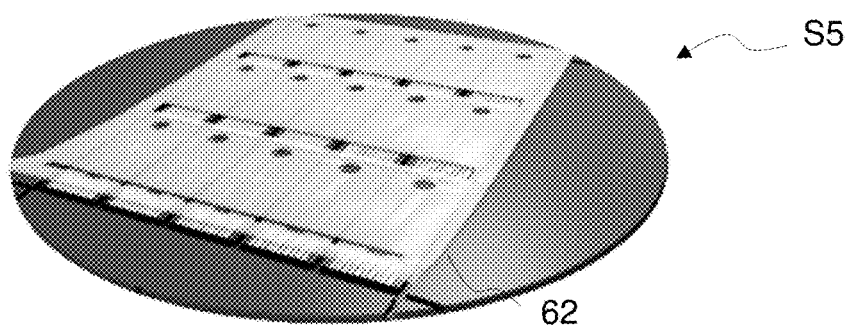
Figure 5:
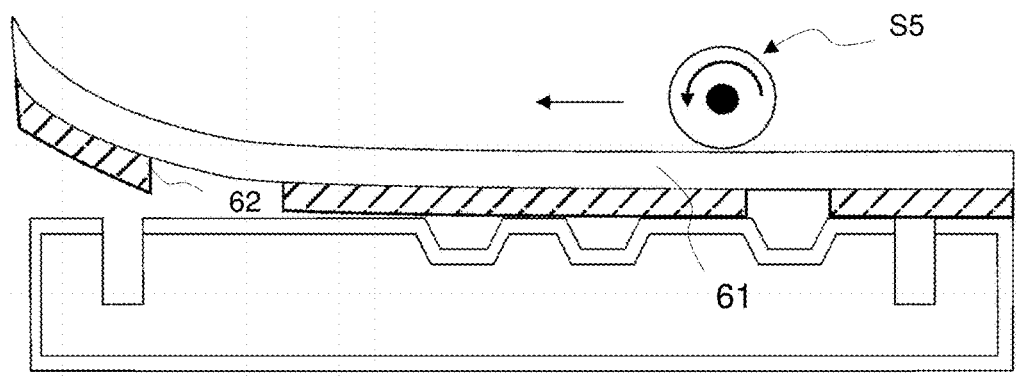

Referring now to FIGS. 3, 5: the cover-film applied S5-S7 may comprise openings 62o that form patterns corresponding to structures of the microfluidic chip assembly, already present or subsequently fabricated. The cover film may thus be designed to favor subsequent fabrication steps of other microfluidic structures like air vents, liquid loading pads, electrical contacts, etc. It incidentally protects the dies too. Exposed surfaces of the assembly 1 may otherwise be protected at an earlier or later stage of the fabrication process, as discussed earlier. Still, any protective film is removed before applying the cover-film 62, which is applied after cutting S2 and before singulation S8. Portions of the film 62 shall typically cover the cuts 10c as well; there is no reason to avoid this since the cover film is chosen so as to allow singulation (that would even substantially complicate the patterning and deposition of the film 62).

Several materials can be contemplated for the cover-film. Preferably yet, the cover-film applied is a dry-film resist 62. In addition, the dry-film resist may preferably comprise an epoxy resin, be a laminate sheet, and/or have a Young's modulus between 3 and 5 gigapascal. Fulfilling any of these conditions contribute to improve characteristics of the cover-film. Polyepoxide films have been found to be best suited for several applications, especially when cleaving the blocks by hand. They notably are rigid enough to tent over microstructures (e.g., microchannels 20) without collapsing, which microstructures typically are 100-200 µm wide. Still, the cover film 62 is brittle enough to allow breaking, and nonetheless has remarkable adhesion to the surface, thereby preventing delamination and leaking. Most practical is to use a cover film initially provided as a laminate sheet to apply it on the surface of the substrate, as discussed below in detail.

In variants, any rigid enough cover film can be contemplated, like silicon or thin glass. The Young's modulus of the cover should typically be between 3 and 200 gigapascal. If an optical clear material is required, glass can be used, but it results in less clean parting breaks, interfaces, etc., than dry-film resists, which usually are optically clear and therefore enable subsequent observation/detection.

For completeness, more sophisticated approaches can be used, such as (i) laminating a dry-film resist on glass, and (ii) then bonding this film/glass layer on microfluidic structures by another lamination step (the dry-film being in contact with the microstructures). The latter approach is interesting for high-pressure fluidic applications where dry-films may not be resistant enough. More generally, one may try to bond any suitable material using an intermediate dry-film adhesive layer.

According to many tests performed by the inventors, best results are obtained if the thickness of the dry-film resist 62 applied is between 10 and 100 µm. Satisfactory results were already obtained with 14 µm thick films but optimal results were obtained for thicknesses of about 50 µm±20 µm. The cover film itself (whatever material it is made of) shall preferably exhibit less than 5% thickness variation, to ensure satisfactory adhesion and sealing.

For instance, a much preferred material is a dry-film resist consisting of 50 µm thick DF-1050 from Engineered Material Systems, Inc. EMS, Ohio, USA, which provides remarkable mechanical performance for applications as discussed herein. This material essentially comprises Epoxy Resin, 6-Glycidyloxynapht-1-yl oxymethyloxirane, and Antmony.

Figure 6:
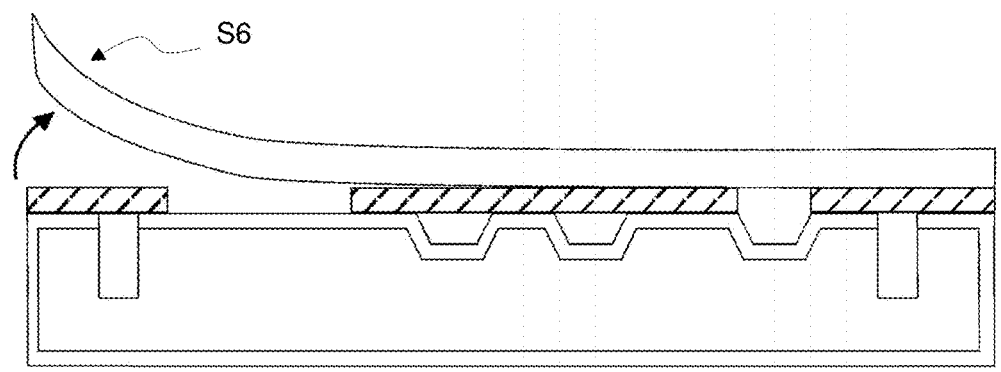
Figure 7:
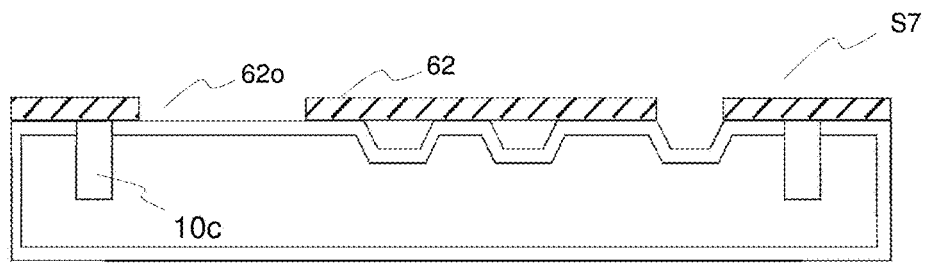
Figure 8:
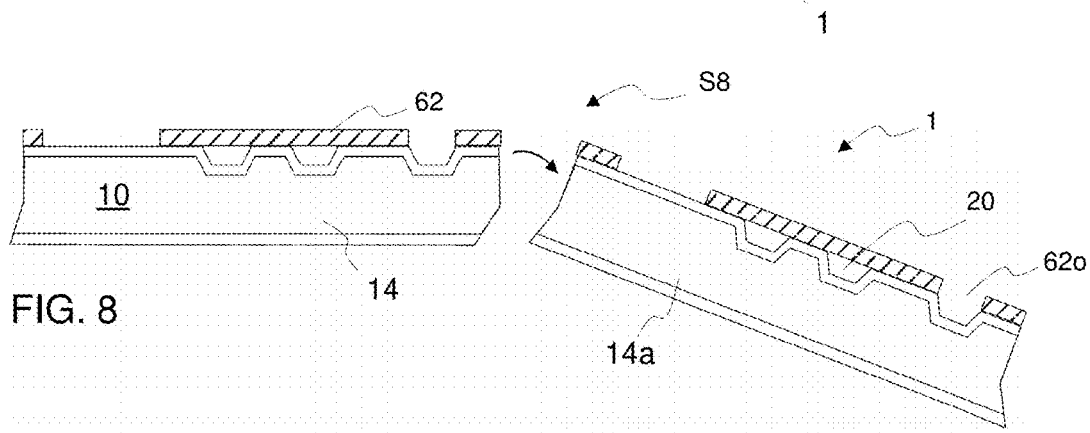

Referring now to FIGS. 5-7, in preferred embodiments, applying S5-S7 the cover film 62 is carried out as follows:
  First, a film 60 is provided S3a-c that comprises at least two layers, i.e., the cover film 62 itself, as well as a backing film 61;
  Second, the cover film 62 is applied S5 against an exposed surface of the substrate (i.e., on said face F), by pressing the backing film 61, preferably by laminating S5 the backing film 61, as illustrated in FIG. 5. "Exposed surface" here means a surface that is accessible for further processing, at a given stage of the fabrication process; and
  Third, the backing film 61 is removed S6.

A practical way of applying the film 62 is indeed to press it indirectly against the surface via another layer 61. Alignment of the dry-film 62 with the chip may be done manually e.g., using markers on both the chip surface and any of the films 61, 62 or thanks to any suitable alignment tool.

Steps S3a-c (FIG. 3) may notably include a step of patterning S3c the cover film 62. This is preferably achieved by photolithography, cutting, punching or laser ablation, and preferably prior to applying S5 the patterned cover film 62. This makes it possible to obtain a cover film 62, e.g., a dry-film resist, that comprises openings 62o forming patterns that correspond to structures of the microfluidic chip assembly, already present or to be subsequently fabricated. That is, the patterns must correspond to, i.e., functionally match features already present 20 or to be later fabricated on the exposed surface of the assembly 1. Of advantage is a dry-film patterned such as to later allow for providing electrical contact openings 62, liquid loading pad, air vents, etc., which features may be fabricated or mounted at a later stage. In some embodiments at least, the patterns correspond to features 20 already present and no additional features are to be fabricated, such that the chips are ready for use after application of the cover-film 62 and after singulation (autonomous chips).

Figure 10:
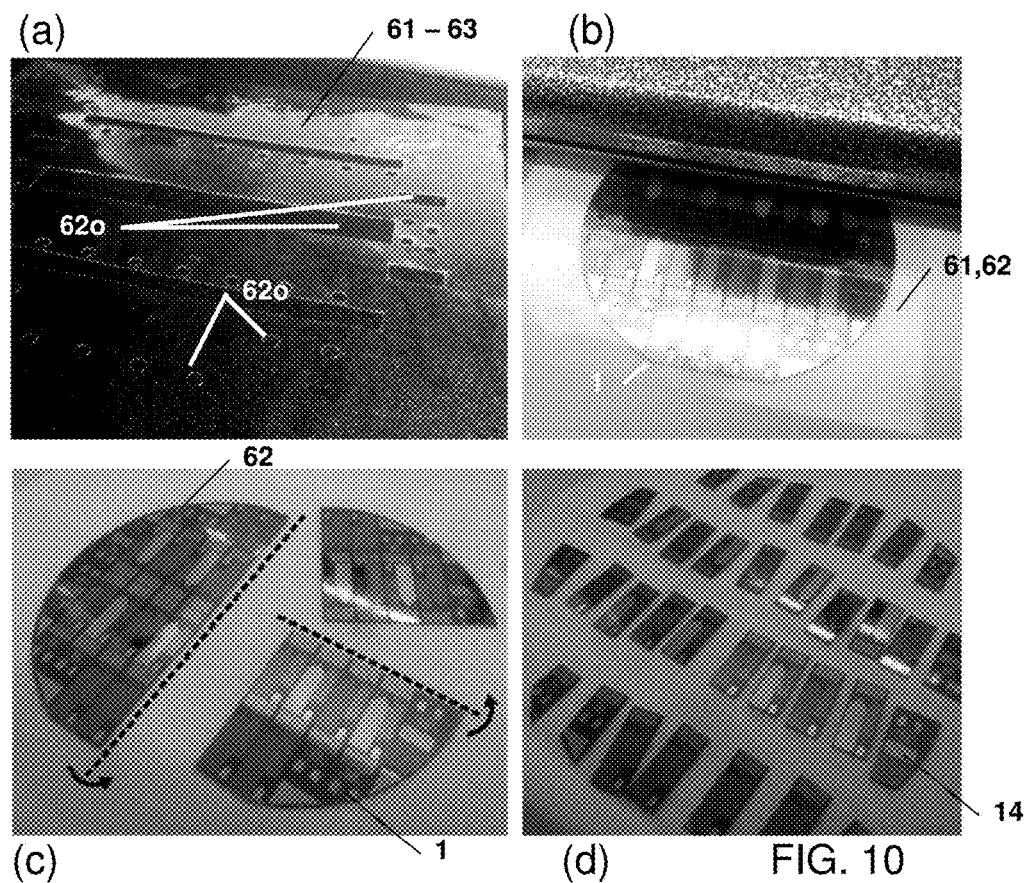
FIGS. 10(a)-(d) are photographs illustrating steps S1, S3, S5 and S8 (also illustrated in FIGS. 1, 3, 5 and 8), respectively, as involved in embodiments. (a) A dry-film resist, patterned using a cutting plotter, is (b) aligned and laminated on a partially diced wafer, which is (c) cleaved by hand, yielding single chips ready for use (d)

As seen in FIGS. 3 and 10, the film 60 may also be initially provided S3*a* as a dry-film resist sandwiched between two backing films 61, 63. One 63 of the two backing films is removed S3*b* prior to or after patterning S3*c* the dry-film resist 62, while the other one of the backing film is kept for lamination. That is, in some variants, the film 63 is removed prior to patterning, while in other variants, the whole stack 61-63 is patterned (contrary to the apparent order in FIG. 3), which may be easier and cleaner, depending on the patterning technique used. Intermediate solutions are also possible. For example:

- If photolithography is used, one would first expose the multi-layer film 61-63 to UV, and then remove a backing film 63 and develop the patterns;
- In case of Laser ablation, the backing film 63 can be removed before laser ablation to reduce the material thickness;
- Using cutting/punching techniques, it is preferred to first cut/punch the stack 61-63 and then remove the backing film 63. In that case, the backing films 61 and 63 protect the dry-film resist 62 when cutting. After forming through holes in the whole sandwich 61-63, the protective film 63 is removed, prior to lamination.

Various methods have been developed for microfluidic chip fabrication, mainly involving rapid prototyping of polymers and silicon or glass micromachining. In general, chips are prepared one-by-one for research purposes or fabricated by wafer-level bonding and then diced. The last fabrication steps usually involve wet media such as cooling water for the dicing saw and require laborious chip handling. Special care is required, in particular when fabricating capillary-driven microfluidic chips because adversary filling of liquids present during the dicing, cleaning, and surface treatment steps can contaminate the channels.

Instead, embodiments of the present invention provide particularly high-throughput microfluidic chip fabrication and singulation, the essential steps being carried out at substrate-level e.g., wafer-level, eliminating tedious chip-by-chip processing. The singulation of the ready-to-use chips may result to be as easy as breaking a chocolate bar.

A particularly preferred embodiment is to partially cut the wafer up to about half the wafer thickness (e.g., 525 µm) using a dicing saw, S2. The partially diced wafer is then cleaned and a pre-patterned dry-film resist 61-62 is aligned and laminated S5 on top of the channels 20. A covered microfluidic body is obtained, S6. Finally, chips can be singulated by breaking through the dicing cuts, S8.

As discussed already, the mechanical properties of the cover film 62 are of particular importance. An ideal cover material 62 should, at least for particular applications, (i) be rigid enough to tent over the channels without collapsing, (ii) be brittle enough to allow breaking, (iii) have good adhesion to the surface to prevent delamination and leaking, (iv) enable patterning by cutting, punching, or photolithography, and (v) not interfere with the wettability of the channels. All these requirements are nicely met with the preferred example of material given above, i.e., a ~50 µm thick DF-1050 from Engineered Material Systems, Inc. EMS.

Concerning now the microchannels: In embodiments, the blocks 14 may notably comprise microfluidic microchannels 20 on face F of the substrate, as part of the microstructures. The average depth or cross-sectional diameter of such microchannels 20 is preferably between 5 and 50 µm, and more preferably between 10 and 20 µm. Still, the microchannel depth is typically constant. On average, a microchannel shall typically have a width between 100-200 µm. Still, a 50 µm width may be used for reduced sections, while up to 500 µm can be contemplated for the wider sections. The channels are typically a few mm long, e.g., 4 mm or more. The channels may be grooved (e.g., etched) into the superficial thickness of the body 10, or a layer 30 adjacent thereto, or provided within a layer covering the body, such as a dry-film resist or a SU-8 film coated and patterned for this purpose, as known per se.

Contrary to usual wafer processing, microfluidics generally have deep structures, i.e. around a few micrometer, up to 20 micrometers or even more. In many cases, 5 micrometers is already considered as a small depth in microfluidic applications. There are multiple reasons: such a small depth can generate a large hydraulic resistance on a liquid and can block or become clogged with microbeads and particles. Such a small depth can also be incompatible with samples containing cells.

Preferred substrates comprise a wafer as a main body 10, e.g., wafers of silicon, germanium, gallium arsenide GaAs, other compound III-V or II-VI materials, as it may allow for benefiting from experience accumulated for integrated circuit IC processes. However, IC processes can usually not be used as such to fabricate microfluidic structures, especially as contemplated herein. Rather, they need be adapted to achieve the typical dimensions required for such structures, as discussed above. In variants, glass can be used as well, instead of semiconductor wafers. Less preferred variants would use other materials such as metals or other materials commonly used in microfluidics.

The wafer may for instance be a <100> Si wafer with a flat in the <110> direction; thus the top surface has a normal in <100> direction. The face F is accordingly parallel to (100) planes in that case, i.e., orthogonal to the (100) direction in the basis of the reciprocal lattice vectors (Diamond structure for Si).

The fabrication methods discussed above may comprise a further step of separating (singulation) at least one of the blocks 14, 14*a* from the package/assembly, to extend to fabrication of individual chips.

Next, according to another aspect, the invention can be embodied as a microfluidic chip package or assembly 1. Consistently with fabrication methods described earlier, such a package/assembly notably comprises:

- A substrate 10, 30, exhibiting one or more blocks 14, 14*a* with microfluidic structures therein. As a result of the partial cut process S2, the substrate 10, 30 exhibits partial cuts 10*c* extending in the thickness of the substrate. The residual thickness of the substrate at the level of these partial cuts 10*c* nevertheless enables singulation of each block 14, 14*a*, preferably by hand; and
- A cover-film 62 covering the blocks. The applied cover film still enables singulation of the covered blocks 14, 14*a*, as discussed above. The cover film 62 is preferably a dry-film resist, e.g., having a thickness between 20 and 100 µm (or more preferably between 30 and 70 µm).

In addition, the cover film 62 may comprise openings 62*o* forming patterns, in correspondence with microfluidic structures of the blocks. Such microfluidic structures may notably comprise:

- an electrical contact opening;
- a liquid loading pad 24; and an air vent.

Such microfluidic chip packages or assemblies can be provided to a recipient, who can then easily singulate the blocks, without any specific equipment, e.g., simply by hand, just as one breaks chocolate bars.

According to a final aspect, the invention can be embodied as a microfluidic chip (obtainable according to present fabrication methods) or, similarly, from a microfluidic chip package or assembly as discussed above. The chip is obtained by separating a covered block 14 from the package or assembly 1. The resulting chip shall therefore exhibit residual marks of partial cut 10c and residual marks of singulation, such as cleavage planes or parting breaks, at a periphery of a covered block. Note that "cleavage", in a broad sense, applies not only to crystalline substrates (e.g., wafers) but also to non-crystalline substrates such as glass wafers. Residual traces of cuts 10c look like a polished mirror surface in the case of Si wafer, see FIG. 11.

The above embodiments have been succinctly described in reference to the accompanying drawings and may accommodate a number of variants. Several combinations of the above features may be contemplated. Examples are given in the next section.

2. Specific Embodiments/Technical Implementation Details

The above concept of microfluidic chip assembly was notably demonstrated as follows: a microfluidic test structure with a loading pad, a serpentine channel 100 µm width, and a capillary pump, was fabricated on a 525 µm thick Si wafer by patterning DuPont PerMX3020 20 µm thick dry-film resist, to pattern microfluidic channels on top of the Si wafer. After coating a thin photoresist layer for protecting the structures, the wafer was diced to about 250 µm depth. A 50 µm thick DF-1050 dry-film resist EMS, USA was cut using a benchtop cutting plotter to create the loading pad and electrical contact openings 62o (FIG. 10a). This cover film was aligned and laminated (FIG. 10b) on the partially diced wafer. Compared to other microfluidic channel sealing techniques such as wafer bonding, the dry-film lamination requires much less time and temperature budget. The sealed chips were then separated easily by cleaving the wafer, FIGS. 10c and d, by hand. Optical inspection of the cleaved chip shows no substantial structural damage on the cover film, see FIG. 11.

Figure 11:
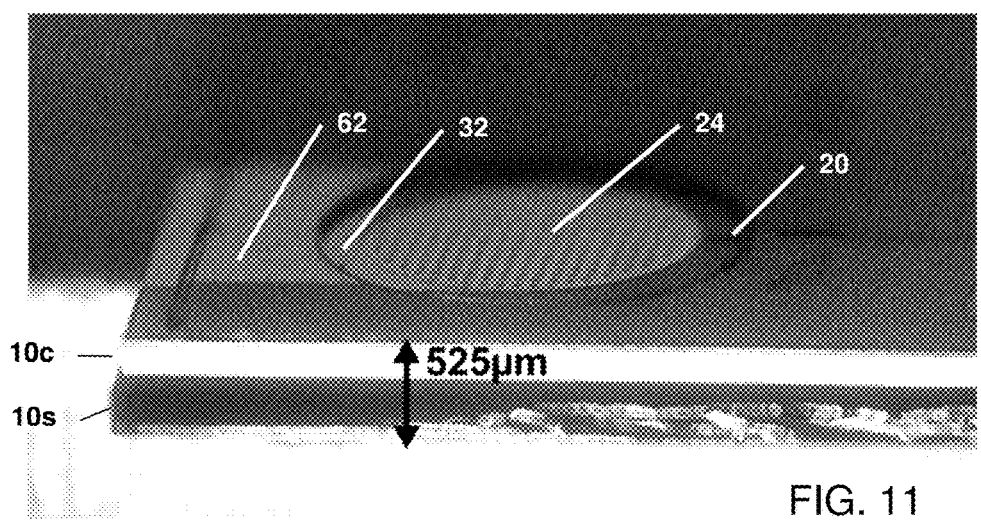
FIG. 11 is an image of a slightly tilted microfluidic chip, showing diced (top) and cleaved (bottom) parts of a microfluidic chip, according to embodiments.

FIG. 11 is an image showing a slightly tilted microfluidic chip, showing a cut (diced) part (top, neighboring partial cut edge 10c) and a cleaved part (bottom, delimited by the cleaved edge 10s) of a microfluidic chip. The chip is in silicon, with microfluidic structures 24 defined in a photopatterned dry-film resist 32 (PerMX3020). Beyond the loading pad 24, the chip comprises a serpentine channel (partly visible) and a capillary pump (not visible). The DF-1050 layer 62 has the slightly larger circular opening (outer circular opening), and is thicker; the PerMX3020 layer 32 has the smaller inner circular pattern, channel 20 is defined in the PerMX3020 layer 32 in this embodiment.

The applicability of the whole process to glass substrates was also tested and verified. How successful the capillary filling of a single chip is can be checked using a colored liquid. Present fabrication concepts are broadly applicable and can impact the entire microfluidic community.

Methods described herein can be used in the fabrication of wafer-based microfluidic chips. The resulting chips can notably be distributed by the fabricator in raw wafer form (that is, as a single wafer that has multiple unpackaged chips), as a bare die, or in a packaged form. In the latter case a chip is mounted in a single chip package (such as a plastic carrier) or in a multichip package. In any case the chip can then be integrated with other chips, or other microfluidic elements (tubing ports, pumps, etc.) even if applications to autonomous chips are preferred, as part of either (a) an intermediate product or (b) an end product.

While the present invention has been described with reference to a limited number of embodiments, variants and the accompanying drawings, it will be understood by those skilled in the art that various changes may be made and equivalents may be substituted without departing from the scope of the present invention. In particular, a feature (device-like or method-like) recited in a given embodiment, variant or shown in a drawing may be combined with or replace another feature in another embodiment, variant or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated. For example, other materials could be used for the cover-film 62.

REFERENCE LIST

1 Microfluidic chip package/assembly
10 Substrate's main body
10, 30 Substrate
10c Partial cuts
10r Residual thickness of substrate at the level of partial cuts 10c
10s Cleaved edge
14, 14a Blocks (chips)
20 Microfluidic structures/microchannels
24 Liquid loading pad
30 Oxide layer
32 Photopatterned dry-film resist
34 Capillary pump
61 Backing film
62 Cover-film
62o Openings

The invention claimed is:
1. A method of fabrication of a microfluidic chip package or assembly (1), comprising:
   providing (S1) a substrate (10, 30) having at least one block (14, 14a) comprising one or more microfluidic structures on a face (F) of the substrate; and
   partially cutting (S2) into the substrate to obtain partial cuts (10c), such that a residual thickness (10r) of the substrate at the level of the partial cuts (10c) enables singulation of said at least one block (14, 14a);
   cleaning (S4) said at least one block; and
   applying (S5-S7) a cover-film (62) to cover said at least one block (14, 14a), whereby at least one covered block is obtained, the applied cover film sealing the microstructures in each said at least one block and still enabling singulation of each covered block, wherein each covered block corresponds to a microfluidic chip after singulation.

2. The method of fabrication of claim 1, wherein
the substrate (10, 30) provided has several blocks (14, 14a), each comprising one or more microfluidic structures on a face (F) of the substrate;
the applied cover-film (62) covers said several blocks (14, 14a); and
the partial cuts (10c) obtained and the cover-film (62) applied are such as to enable singulation of each of said several blocks (14).

3. The method of fabrication of claim 1, wherein partially cutting (S2) into the substrate is carried out such that a residual thickness of the substrate after partially cutting makes it possible to separate said at least one block (14) by hand, preferably by cleaving said at least one block (14).

4. The method of claim 1, wherein the cover-film applied (S5-S7) comprises openings (62o) forming patterns corresponding to structures of the microfluidic chip assembly already present or to be subsequently fabricated.

5. The method of claim 4, wherein the cover-film applied (S5-S7) is a dry-film resist (62), and wherein, preferably, the cover-film fulfills one or more of the following conditions: it comprises an epoxy resin, it is a laminate sheet, and has a Young's modulus between 3 and 5 gigapascal.

6. The method of claim 4, wherein a thickness of the dry-film resist (62) applied is between 10 and 100 μm, and preferably between 30 and 70 μm.

7. The method of claim 4, wherein applying (S5-S7) the cover film (62) comprises:
providing (S3a-c) a film (60) comprising at least two layers, including the cover film (62) and a backing film (61);
applying (S5) the cover film (62) against an exposed surface on said face (F) of the substrate by pressing the backing film (61), preferably by laminating (S5) the backing film (61); and
removing (S6) the backing film (61).

8. The method of claim 7, wherein providing (S3a-c) the film (60) further comprises patterning (S3c) the cover film (62), preferably by one of: photolithography; cutting; punching; or laser ablation, prior to applying (S5) the patterned cover film (62), to obtain a cover film (62) that comprises openings (62o) forming patterns corresponding to structures of the microfluidic chip assembly already present or to be subsequently fabricated.

9. The method of claim 1, wherein at least one block (14) of the substrate provided exhibits a microfluidic microchannel (20) on said face (F), the average depth or cross-sectional diameter of the microchannel (20) being between 5 and 50 micrometers, and preferably between 10 and 20 micrometers.

10. The method of fabrication of claim 1, wherein the method further comprises, after cleaning (S4) and before applying (S5-S7) the cover-film, a step (S4a) of depositing reagents in one or more of the microfluidic structures (20), wherein depositing reagents preferably comprises depositing at least two types of reagents in microfluidic structures of at least two different blocks (14, 14a) of the substrate, respectively, or within one or more microstructures (20) of a same block (14, 14a).

* * * * *